United States Patent [19]

Brauer et al.

[11] Patent Number: 4,599,891

[45] Date of Patent: Jul. 15, 1986

[54] TCH—TRI-AXIAL CORE HOLDER

[75] Inventors: Paul R. Brauer, Tulsa; Thomas J. Barnickel; Gary C. Mast, both of Broken Arrow, all of Okla.

[73] Assignee: Temco, Inc., Tulsa, Okla.

[21] Appl. No.: 618,039

[22] Filed: Jun. 7, 1984

[51] Int. Cl.⁴ .................................. G01N 15/08
[52] U.S. Cl. ................................. 73/38; 73/819
[58] Field of Search ............... 73/38, 37, 819, 84

[56] References Cited

U.S. PATENT DOCUMENTS

| | | | |
|---|---|---|---|
| 2,345,935 | 4/1944 | Hassler | 73/38 |
| 2,705,418 | 4/1955 | Reichertz et al. | 73/38 |
| 2,842,958 | 7/1958 | Sayre, Jr. et al. | 73/38 |
| 3,457,777 | 7/1969 | Nielsen | 73/84 |
| 3,616,685 | 11/1971 | Strom | 73/819 X |
| 3,839,899 | 10/1974 | McMillen | 73/38 |
| 4,253,327 | 3/1981 | Wiley | 73/38 |

Primary Examiner—Stewart J. Levy
Assistant Examiner—Joseph W. Roskos
Attorney, Agent, or Firm—Head, Johnson & Stevenson

[57] ABSTRACT

A core holder is described which shows a rock core in a resilient sleeve within a hollow housing. A longitudinal axial force is applied on the core independently of pressure applied radially on the core. Fluid pressure or flow is measured at the periphery of the core during injection of fluids therethrough while various pressures are independently applied at infinitely variable degrees of radial and longitudinal axial forces.

6 Claims, 4 Drawing Figures

TCH—TRI-AXIAL CORE HOLDER

BACKGROUND OF THE INVENTION

1. Field of the Invention

The present invention relates to an apparatus for holding a core normally cut from a rock taken from a subsurface terrain. The core holder permits various measurements to be made on the core so that certain of its physical properties can be determined.

2. Background of the Invention

In the oil and gas industry holes are drilled in the earth to sub-surface formations which may be productive of oil, gas or minerals and frequently cores are cut from these formations suspected to contain oil or gas. The core may be of various sizes, e.g. $\frac{3}{4}'' \times 2''$ long. For these cores to be of any value they must be analyzed to determine various physical properties of the rock from which it was cut. Such properties are measured for permability, porosity, fluid flow and fluid and/or gas saturations.

SUMMARY OF THE PRESENT INVENTION

The present invention relates to a tri-axial core holder which includes a hollow housing preferably made of steel, having a resilient sleeve therein. The core to be analyzed is inserted into the resilient sleeve. In the preferred embodment a fixed plug means close off one end of the sleeve and a second plug means moveable within the hollow housing closes the other end. Means are provided to convey fluids through a passage in the moveable means to one end of the core so that fluid may pass through the core and out passage means in the fixed plug means closing the other end of the sleeve. Port means are provided in the walls of the housing and resilient sleeve so that fluid pressure from a first pressure source can be applied against the outer wall of the sleeve forcing the sleeve firmly against the core. This also is a means of providing radial pressure or force on the core being examined.

Second pressure source independant of the first pressure source is provided for applying axial pressure on the second cap means which puts axial longitudinal force on the core. Fluid can then be passed through the core with the core under any desired lateral or axial stress and temperature. This also permits automatic compensation for core length variations without resorting to the use of spacers.

DESCRIPTION OF THE DRAWINGS

A better understanding and a fuller description of the present invention will appear in connection with the detailed description of the drawings in which.

DESCRIPTION OF THE PREFERRED EMBODIMENT

Figure 1:
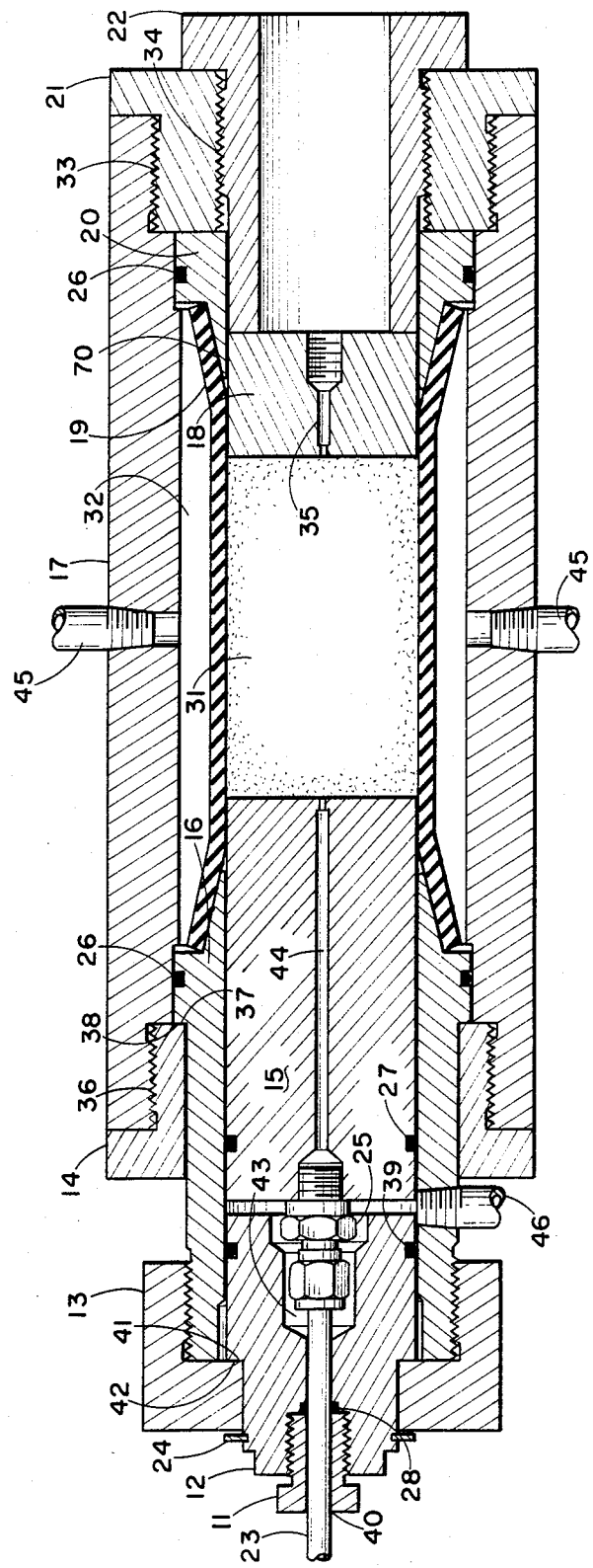
FIG. 1 is a plan view, partly in section of one embodiment of the core holder of this invention.

We refer first to FIG. 1. Shown thereon is a housing 17 having a central passage 32. Mounted within the housing is sleeve 19 which preferably is made of an elastomer. However, other resilient material may be used. One end of sleeve 19 is stretched outwardly over shoulder 70 of ferrule 20 which is secured in one end of the hollow housing 17. It is held in place by a plug 21 having external threads 33 which are threaded to the housing 17. An O-ring seal 26 is provided between ferrule 20 and the housing. A retainer 22 is screwed into internal threads 34 of plug 21. A fixed plug 18 is held in position inside sleeve 19 at one end thereof by retainer 22. A passage 35 extends axially through fixed plug 18.

Attention is next directed to the opposite end 15 of housing 17 from fixed plug 18. There we have a moveable plug 15 which is inside a long ferrule 16 which has O-rings 26 sealing with the housing. A hollow plug 14 is threadably connected by threads 36 to the housing 17 and has a shoulder 37 which abutts against shoulder 38 of the long ferrule 16 to hold it in position. Moveable plug 15 has O-ring seal 27 for sealing with the interior surface of the bore of ferrule 16.

Means will now be discussed for holding moveable plug 27 in position. This includes a cap 13 which is threadably connected to long ferrule 16. A plug 12 having a longitudinal passage is held inside long ferrule 16 by shoulder 41 of cap 13 which abutts against shoulder 42 of plug 12.

Means will now be discussed for the part of the apparatus which permits fluid to be injected through the moving plug 15 to the face of core 31. This includes a tube 23 which is inserted through plug 11 which is connected by threads to plug 12. (Longitudinal passage 40 extends through plus 11 and 12. Tube 23 extends through passage 40 into cavity 43 within plug 12 where it is connected by any known tube fitting connector such as a Swagelok SS-400-1-OR to a passage 44 in moveable plug 15. Seals 28 are provided between plug 12 and tubing 23. With this arrangement as plug 15 moves tubing 23 can also pass through seal 28 and the connectors 25 also moves with the moveable plug 15.

There are means provided for applying a radial force to sleeve 19. This includes one or more port means and conduits 45 which extend through the wall of the housing. Fluid, which may be either gas or liquid, is applied through conduit means 45 against the outer wall of the sleeve 19 under any selected pressure. Means are also provided for applying an independent longitudinally axial force against core 31. This includes a conduit means 46 which extends through the wall of long ferrule 16 and is in communication with the space between moveable plug 15 and plug 12. This space is sealed by seals 27 and 39. Fluid from a source not shown is directed through conduit means 46 to drive moveable plug 15 against the core 31. Any selected pressure can be used here.

It is most important to note that the fluid pressure applied against the moveable plug 15 is independant of fluid pressure which is applied laterally against sleeve 19. One can therefore readily vary the longitudinally axial load on the core without changing or modifying any force which may be applied radially on the core through sleeve 19. Likewise one may readily change the radial force applied through sleeve 19 on the core 31 without changing the longitudinally axial force applied on the core. Or alternately one may readily modify simultaneously the radial force and the longitudinally axial force applied on the core. This has been found to be very important in studying the physical characteristics of the core under various conditions.

It is quite easy to remove core 31 and insert another one therein. All that is necessary is to remove retainer 22 from plus 21. Then fixed plug 18 and core 31 can readily be removed. If desired a vacuum pump may be attached to port means 45 so that sleeve 19 will expand away from core 31 to make removal of the core easier. Another core can then be inserted and fixed plug 18 reinserted and retainer 22 connected to plug 21. Then the device is ready for additional assertion of pressure on the core in the same manner as described above.

Figure 2:
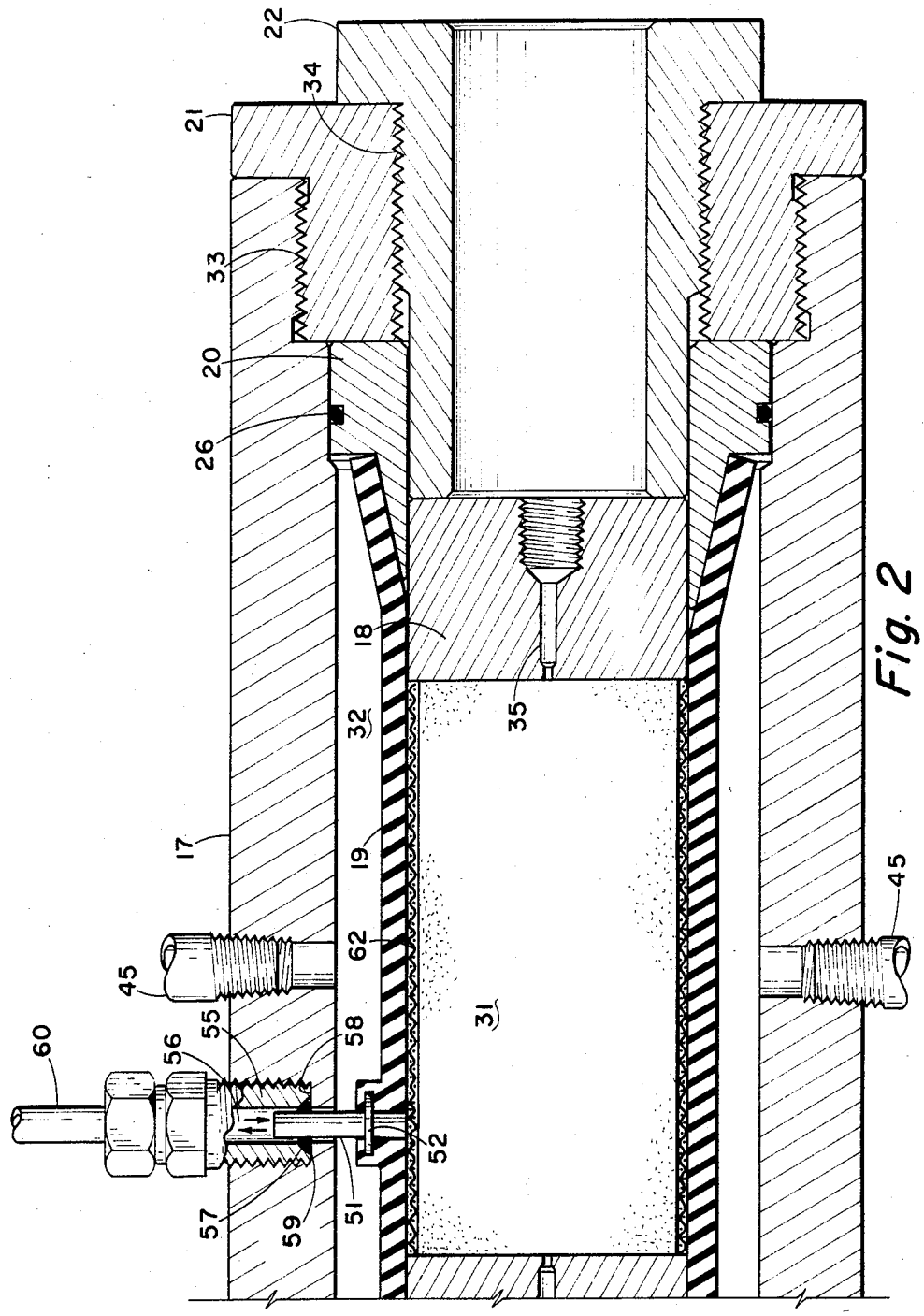
FIG. 2 is a partial view of FIG. 1 of a modification showing means for determining the pressure or fluid flow within the sleeve of the core holder.

Sometimes when an analysis is made on a core it is desired to know the pressure, temperature, or obtain a sample of the fluids at various positions along the core. FIG. 2 illustrates a modification of that device of FIG. 1 which permits this to be accomplished. Only that portion of the device adjacent the core and sleeve of FIG. 2 has been reproduced as FIG. 2 inasmuch as the remaining portion of the apparatus of FIG. 1 may be the same. Molded into sleeve 19 is a radial tube 51 which has a base 52 which as shown FIG. 3 has a plurality of vertical holes 53. This base 52 is molded into the elastomer of sleeve 19 using known molding procedures. The molded rubber or elastomer is also in holes 53 and this increases the effective shear strength of plate 52 so that tube 51 is held securely in place. A hollow plug 55 having central passage 56 is screwed into a passage through the wall of housing 17. The lower end of plug 55 has shoulder 57 which together with shoulder 58 of the passage through housing 17 provides a seat for seal 59 which may be O-rings. The outer end of plug 55 is connected to a tubing 60 in any known manner. The tubing 60 is connected to pressure or temperature measuring or fluid sampling system means. Tube 51 can move through passage 56 of plug 55 and maintain a seal with O-rings 59. This movement is very important inasmuch as the housing 17 is rigid and sleeve 19 is moveable due to the pressure applied in annulus 32 through conduit means 35. Any desired number of the pressure, temperature or fluid sensing means of FIG. 2 can be applied at any desired position about sleeve 19 and housing 17. This permits a wide variety of pressure, temperature or fluid measurements to be made while the fluid is flowing through the core 31 and also while various radial and various longitudinal axial forces are applied to the core 31. This permits a very wide range of pressure and fluid flow measurements to be made on any core which may be placed in the core holder. This is very important in research and in reservoir engineering which is a science of fluid flow and fluid recovery in underground rock formations.

Figure 3:
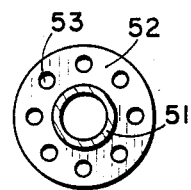
FIG. 3 illustrates the base of the probe of the modification of FIG. 2 which is molded into the sleeve.

In connection with the obtaining of a pressure or fluid flow at various points as shown by FIG. 3 it is sometimes desireable that the fluid flow be something other than a point pressure. This can be obtained by using a screen 62 as shown in FIG. 2. This permits the determination of the flow in a larger surface area of the surface of the core.

Figure 4:
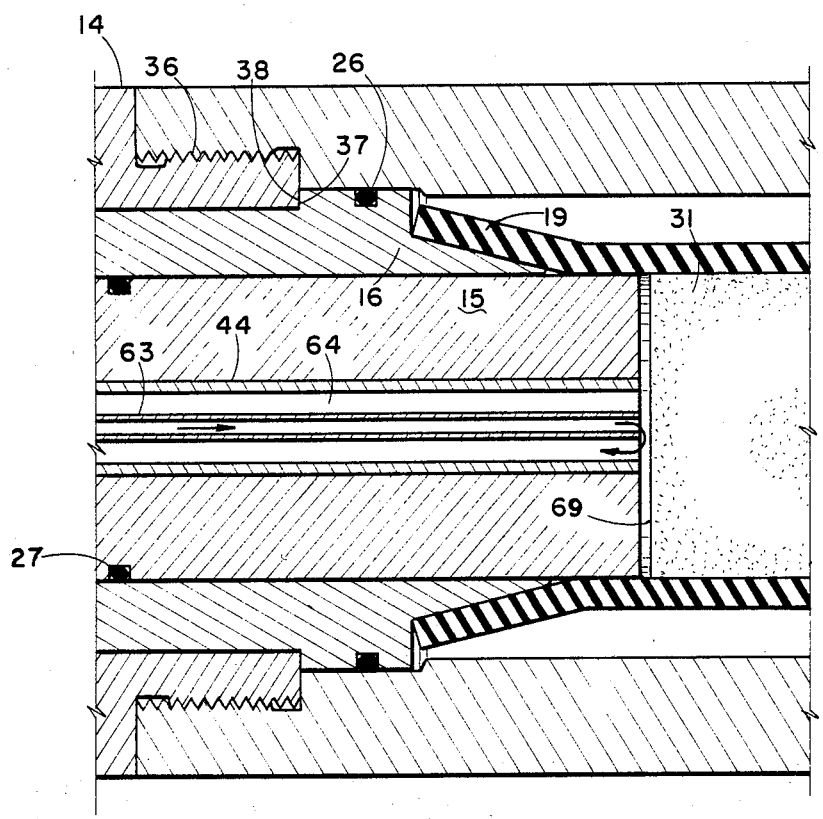
FIG. 4 illustrates concentric tubes for conveying fluid to the core and for determining pressure at the core injection face.

Sometimes it is desired to wash the injection face of core 31. This can be accomplished by the device of FIG. 4. Shown therein there is an interior tubing 63 which is inside tubing 44A. These may be concentric tubings. If it is desired to wash a portion of the face 64 of core 31 fluids can be injected through tubing 63 across the face 69 and back through the annulus 64 between tubing 44 and 63.

Sometimes it is desired to measure the injection pressure at the face of core 21. This can be accomplished by the device of FIG. 4. Shown therein there is an interior tubing 63 which is inside tubing 44A. These may be concentric tubings. If it is desired to measure the pressure at the face 69 of core 31 the pressure can be measured through the annulus 64 between tubing 44A and 63. This is important because one is not measuring the pressure drop in the injection fluid tube 63.

While the invention has been described with a certain degree of particularity it is manifest that many changes may be made in the details of construction and the arrangement of components without departing from the spirit and scope of this disclosure. It is understood that the invention is not limited to the embodyments set forth herein for purposes of exemplification, but is limited only by the scope of the attached claim or claims, including the full range of equivalency to which each element thereof is entitled.

What is claimed is:

1. A tri-axial core holder comprising:
   a hollow housing;
   a resilient sleeve within said housing;
   first means closing one end of said sleeve;
   second means closing the other end of such sleeve and movable therein;
   first pressure means for applying radial pressure on said sleeve;
   second pressure means for applying pressure on said second means in a direction of the longitudinal axis of said sleeve independently of the radial pressure on said sleeve;
   fluid passages through said first and second means including concentric tubings so that fluid can be inserted through the smaller of such concentric tubings and returned through the annulus between the tubings, two different fluids can be inserted simultaneously or pressure can be monitored at the face of the core when inserted.

2. A tri-axial core holder comprising:
   a hollow housing;
   a resilient sleeve within said housing;
   first means closing one end of said sleeve;
   second means closing the other end of such sleeve and movable therein;
   first pressure means for applying radial pressure on said sleeve;
   second pressure means for applying pressure on said second means in a direction of the longitudinal axis of said sleeve independently of the radial pressure on said sleeve;
   at least one fluid passage extending through said sleeve and said housing.

3. A core holder as defined in claim 2 in which said fluid passage includes:
   a lateral tubing extending through said sleeve and protruding outwardly into an opening in said housing; and
   a seal means in said opening sealingly engaging the exterior surface of said lateral tubing permitting radial movement of said tubing with respect to said housing.

4. A tri-axial core holder comprising:
   a hollow housing;
   a resilient sleeve within said housing;
   first means closing one end of said sleeve;
   second means closing the other end of such sleeve and movable therein;

first pressure means for applying radial pressure on said sleeve;

second pressure means for applying pressure on said second means in a direction of the longitudinal axis of said sleeve independently of the radial pressure on said sleeve;

an end cap for said housing adjacent said second means and;

a fluid conveying tubing movably extending through said end cap and extending through and movable with said second means, so variable length cores are accommodated.

5. A core holder as defined in claim 4 including a cylindrical screen means inside said sleeve.

6. A tri-axial core holder comprising:

a hollow housing;

a resilient sleeve within said housing;

first means closing one end of said sleeve;

second means closing the other end of such sleeve and movable therein;

first pressure means for applying radial pressure on said sleeve;

second pressure means for applying pressure on said second means in a direction of the longitudinal axis of said sleeve independently of the radial pressure on said sleeve;

an end cap extending through and movable with said second means.

* * * * *